(12) United States Patent
Suh et al.

(10) Patent No.: US 6,585,666 B2
(45) Date of Patent: Jul. 1, 2003

(54) ARTHROSCOPIC DIAGNOSTIC PROBE TO MEASURE MECHANICAL PROPERTIES OF ARTICULAR CARTILAGE

(75) Inventors: Jun-kyo Suh, Pittsburgh, PA (US); Freddie H. Fu, Pittsburgh, PA (US); Inchan Youn, Pittsburgh, PA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 0 days.

(21) Appl. No.: 09/916,649

(22) Filed: Jul. 30, 2001

(65) Prior Publication Data

US 2002/0049382 A1 Apr. 25, 2002

Related U.S. Application Data

(63) Continuation of application No. 09/417,970, filed on Oct. 13, 1999, now abandoned.
(60) Provisional application No. 60/103,905, filed on Oct. 13, 1998.

(51) Int. Cl.$^7$ .............................................. A61B 5/103
(52) U.S. Cl. ..................... 600/587; 600/443; 600/449; 600/459; 600/462; 702/41; 702/43; 73/573
(58) Field of Search ................................ 600/437–447, 600/449–467, 587

(56) References Cited

U.S. PATENT DOCUMENTS

| | | | |
|---|---|---|---|
| 4,364,399 A | | 12/1982 | Dashefsky ................... 128/774 |
| 5,433,215 A | * | 7/1995 | Athanasiou et al. ........ 600/587 |
| 5,503,162 A | | 4/1996 | Athanasion et al. ........ 128/774 |
| 5,766,137 A | * | 6/1998 | Omata ........................ 600/587 |

OTHER PUBLICATIONS

Kellgren et al.; "Radiological Assessment of Osteo–Arthrosis"; Annals of the Rheumatic Diseases; vol. 16; 1957; pp. 494–502.

Myers et al.; "Experimental Assessment by High Frequency Ultrasound of Articular Cartilage Thickness and Osteoarthritic Changes" The Journal of Rheumatology; vol. 22, No. 1; 1995; pp. 109–116.

Jurvelin et al., "Comparison of Optical, Needle Probe and Ultrasonic Techniques for the measurement of Articular Cartilage Thickness", 3 Biomechanics, pp. 231–235 (1995).

Lyyra et al., "Indentation Instrument for the Measurement of Cartilage Stiffness Under Arthroscopic Control", 17 Med. Eng. Phys., pp. 395–399 (1995).

* cited by examiner

Primary Examiner—Marvin M. Lateef
Assistant Examiner—Ruby Jain
(74) Attorney, Agent, or Firm—Foley & Lardner

(57) ABSTRACT

A mechanical diagnostic probe is used to determine the thickness of articular cartilage, so that any degeneration in the articular cartilage can be detected at an early stage. The probe advantageously allows for calibrating the speed of the ultrasound in situ thereby allowing for more accurate measurements of the tissue thickness. The probe also can be used to monitor the condition of the cartilage after surgery and/or after or during physical rehabilitation of the cartilage. The probe is comprised of a probe handle and a probe, which is comprised of an ultrasonic transducer, strain-gauges, and a linear displacement actuator. A predetermined displacement then is applied to the indenter tip and a computer program is then used to analyze the results.

20 Claims, 17 Drawing Sheets

ARTHROSCOPIC DIAGNOSTIC PROBE TO MEASURE MECHANICAL PROPERTIES OF ARTICULAR CARTILAGE

This application is a continuation of application Ser. No. 09/417,920, filed Oct. 13, 1999, which in turn is based on provisional application 60/103,905 filed Oct. 13, 1998.

BACKGROUND OF THE INVENTION

1. Field of the Invention

The arthroscopic diagnostic mechanical probe of the present invention is a computer-controlled indentation test device for articular cartilage. It provides clinicians with quantitative mechanical diagnostic data for cartilage.

Articular cartilage is an avascular soft tissue that covers the articulating bony ends of joints. During joint motion, cartilage acts as a lubricating mechanism in the articulating joints and protects the underlying bony structure by minimizing peak contact force at the joint. The mechanically superior capacity of articular cartilage, as a lubrication bearing as well as a viscoelastic shock absorber, is attributable to the structural integrity of its molecular constituents and their interactions with synovial fluid.

Once damaged, however, articular cartilage has limited or no ability to heal and often degenerates, leading to a degenerative joint disease call osteoarthritis ["OA"]. The most evident characteristics of OA are the loss of cartilage itself, from the joint surface, and the formation of osteophytes around the articular margin of the bony structure of the joint. Such degenerative changes usually are initiated by mechanical damage of the cartilage matrix, primarily manifested by a rupture of the dense collagen meshwork, a decrease of the proteoglycan ["PG"] content of the tissue, and an increase of the interstitial fluid content. As a result, the articular cartilage becomes softer and loses its normal mechanical properties, resulting in an abnormal stress/strain field in the extracellular matrix ["ECM"]. The altered mechanical properties of cartilage creates an abnormal mechanical environment around the chondrocytes. In turn, this triggers an aberrant metabolic behavior of chondrocytes, producing a variety of matrix-destructive cycles, consisting of mechanical wear and tear of the cartilage matrix and the catabolic activities of chondrocytes of OA.

A change in the mechanical properties of articular cartilage can be considered the first detectable sign of cartilage degeneration. Some animal studies have shown that changes in the mechanical properties of articular cartilage can be used as a more sensitive indicator of early degeneration than the histological grading system. An efficient way, therefore, to prevent such osteoarthritic degeneration of cartilage entails early detection of mechanical changes in articular cartilage. Early detection will provide an opportunity to treat the patient at an early stage prior to occurrence of the aforementioned irreversible tissue damage.

2. Description of the Related Art

At present, there are two main diagnostic classification systems for osteoarthritic cartilage. The Kellgren and Lawrence grading system, Kellgren, J. H. and Lawrence, J. S., *radialogical Assessment of Osteoarthrosis*, 16 Ann. Rheum. Dis. 494–502 (1957), is based solely on radiographic grading, while the American College of Rheumatology criteria involves a mixture of clinical and radiographic features of joints. Both systems have been criticized for a lack of sensitivity, objectivity, and reproducibility. The absence of an accurate and objective diagnostic tool for articular cartilage may engender in inconsistent epidemiological conclusions, inconsistent identification of risk factors, and slowed development of primary preventive strategies for OA.

Dahefsky, U.S. Pat. No. 4,364,399, designed a diagnostic instrument to measure the deformation resistance of tissue, particularly the articular surface of the patella. The Dahefsky measurement surface utilized a special elastomeric indenter to measure the deformation resistance force of the articular cartilage. The measured reaction force, therefore, is not a pure function of cartilage stiffness, but a combined function of the material properties of the articular cartilage and the elastomeric indenter.

More recently, Lyyra T., et al., *Indentation Instrument for the Measurement of Cartilage Stiffness Under Arthroscopic Control*, 17 Med. Eng. Phys. 395–99 (1995), developed an arthroscopic indentation instrument (Artscan 1000) to evaluate the elastic stiffness of cartilage. Using the Lyyra instrument, the cartilage surface is indented by a given displacement and the indenter force is measured and then used to represent the tissue stiffness. The instrument, however, is unable to measure the cartilage thickness. Without the thickness data of articular cartilage, the true mechanical properties of the tissue cannot be obtained. Their instrument is also unable to measure the viscoelastic characteristics of articular cartilage. Viscoelasticity is the primary mechanism responsible for impact energy dissipation. The viscoelastic property, therefore, is critically important for assessing the mechanical condition of articular cartilage and is a sensitive indicator of degenerative alterations in the tissue structure. Moreover, the Lyyra system is very susceptible to human error because the indenter is manually pushed to the cartilage surface via a handheld instrument.

Athanasiou, U.S. Pat. Nos. 5,433,215 and 5,503,162, proposed an improved arthroscopic indentation probe capable of measuring the viscoelastic properties of articular cartilage. They also incorporated a tissue measurement technique using a penetrating probe method in their arthroscopic instrument. However, the penetrating needle probe can cause permanent structural damage to the articular cartilage.

All of these devices fail in a commonly important respect. None allow for a nondestructive accurate measurement of cartilage thickness during the arthroscopic mechanical probing procedure in situ. This, in turn, hampers the effectiveness of the probing devices because an accurate measurement of the thickness is necessary to quantitatively determine the tissue's inherent mechanical properties. In fact, several studies have reported the feasibility of a high frequency ultrasonic transducer to measure the thickness of articular cartilage. It was found, however, that the accuracy of the ultrasonic thickness measurement of cartilage was limited by the fact that that the ultrasound speed in the cartilage could not be measured in situ and had to be assumed a priori. Jurvelin, J. S., et al., *Comparison of Optical, Needle Probe and Ultrasonic Techniques for the Measurement of Articular Cartilage Thickness*, 3 Biomechanics 231–35 (1995). An inaccurate estimation of cartilage thickness will result in erroneous data about the mechanical properties of articular cartilage.

SUMMARY OF THE INVENTION

An object of the invention to provide a probe which can be used to monitor cartilage condition before irreversible degenerative changes develop in articular cartilage, as well as to monitor cartilage condition after damaged cartilage has been surgically repaired and undergone physical therapy.

Another object of the invention is to provide a method and apparatus for calibrating the speed of the ultrasound in situ.

Yet another object of the invention is to provide a method and an apparatus to monitor and measure the viscoelastic properties of articular cartilage.

A further object of the invention is to provide a method and an apparatus to monitor articular cartilage while preventing damage to the cartilage.

Yet a further object of the invention is to provide a method and an apparatus which minimizes human error.

To achieve these objects, the invention provides for a method for examining articular cartilage, comprising:
(a) contacting a surface of articular cartilage with an ultrasonic transducer;
(b) applying a predetermined displacement, $d_s$, to said surface; and
(c) determining a thickness of said articular cartilage as a function of the true ultrasound speed thereof, $v_s$, which is defined by the equation:

$$v_s = 2d_s/(t_1 - t_2)$$

wherein $t_1$ is the echo time before applying said predetermined distance and $t_2$ is the echo time after applying said predetermined distance.

The invention then allows the thickness, h, of the tissue to be calculated using the following function, although there are others:

$$h = v_s * t_1/2$$

The invention also encompasses a diagnostic probe for articular cartilage, comprising (A) a probe handle and (B) a probe shaft, fixed to said handle; that comprises a housing cylinder having a proximal end and a distal end, wherein said probe shaft further comprises, from distal to proximal, (i) an ultrasonic transducer attached at the distal end of said housing cylinder; (ii) a plurality of strain-gauges attached to said housing cylinder; and (iii) a linear displacement actuator which is displaceably mounted to said housing cylinder.

DETAILED DESCRIPTION OF THE PREFERRED EMBODIMENT

A probe within the present invention employs a displacement control mechanism with an ultrasonic transducer to obtain the thickness of articular cartilage by measuring accurately the true speed of sound in the articular cartilage in situ. Using a plurality of strain-gauges attached to the displacement actuator, the probe also measures the reaction force of articular cartilage, as a function of time, under a given indentation displacement. The measured tissue thickness data and the indentation reaction force data are used to quantify the mechanical properties of articular cartilage.

The ultrasound indentation technique of the present invention is easily adaptable to an arthroscopic probe, because a miniature ultrasound transducer preferably is employed as an indenter tip of the probing instrument. By implementing a ramping indentation of a given displacement to the indentation probe, the instrument will provide an accurate measurement of tissue thickness and indentation stiffness of articular cartilage. This permits an evaluation of the mechanical properties of articular cartilage during arthroscopic diagnosis, and a precise classification of the pathological conditions of articular cartilage.

The present invention is further illustrated by reference to the following example, which is not to be taken as limiting of the invention, in its broadest aspects.

Tests and Data

Tests with the subject method were conducted and the results follow:

Specimen Preparation

Forty osteochondral plugs (1 cm×1 cm×1 cm) having a normal appearance were obtained from the facets of patellar groove and the femoral condyles of ten young fresh bovine knee joints. Specimens were wrapped with saline gauge and stored at −20° C. before experiments. All of the experiments were completed within two weeks after harvesting the specimens.

Twenty specimens were used to validate the accuracy of the in situ calibration technique to measure the thickness of articular cartilage, as described below. The remaining twenty specimens were used to measure the indentation stiffness of normal and proteoglycan-depleted OA-like cartilage, as described below.

In Situ Calibration Method and Cartilage Thickness Measurement

Figure 8:
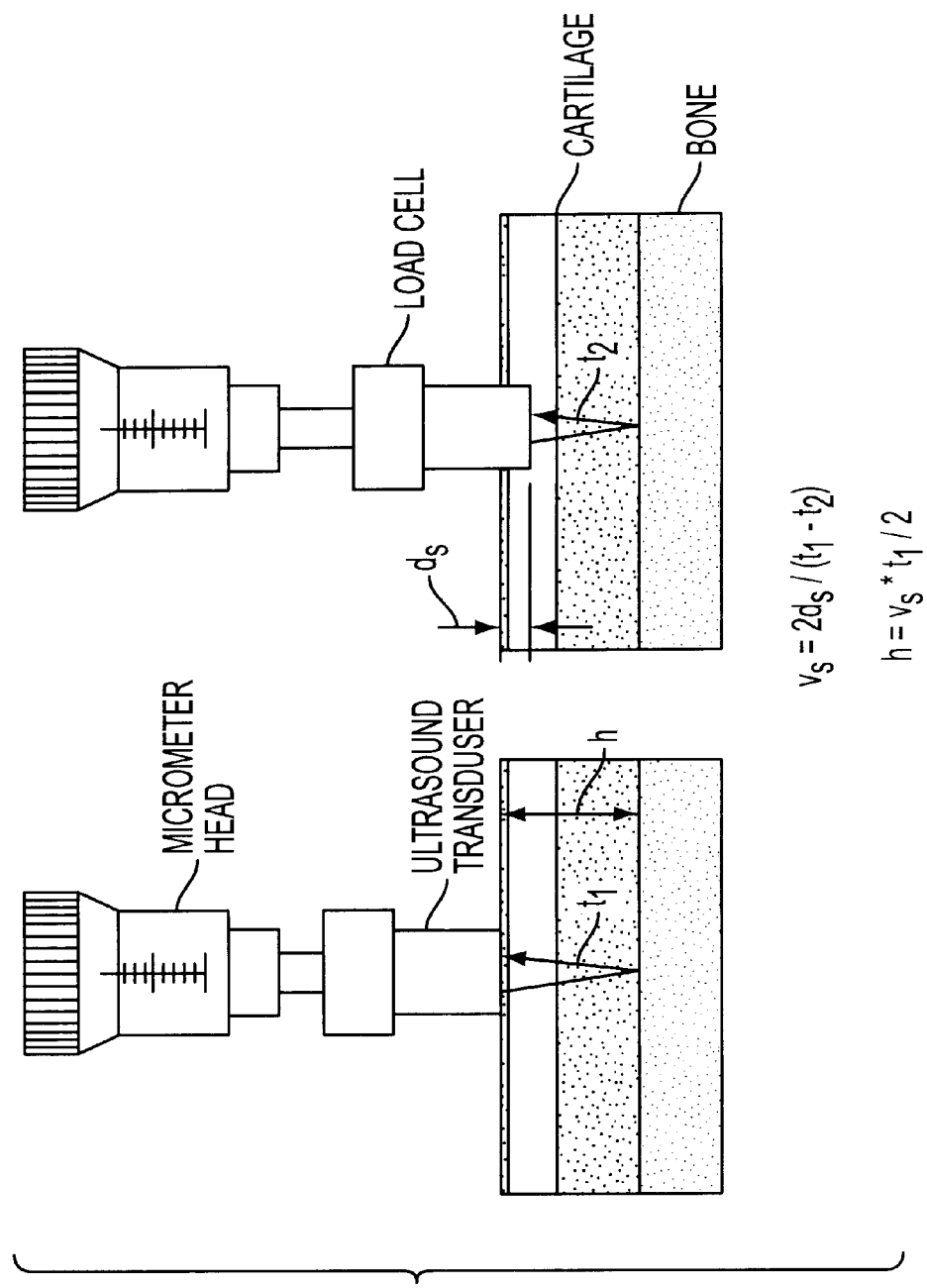
FIG. 8 shows how the thickness of the articular cartilage is determined.

The articular cartilage thickness (from cartilage surface to tidemark) was measured using a miniature ultrasonic contact transducer, in this example, a 3 mm diameter, XMS-310, 10 MHz transducer manufactured by Parametrics Inc (Waltham, Md.) was used. An initial contact was first made between the ultrasound transducer and the cartilage surface by applying a preload of 0.5 g to the transducer. The preload was measured through a load cell, that is, a plurality of strain-gauges. After the pre-loading condition was equilibrated, the transducer was then displaced by a pre-determined distance ($d_s$) using a micrometer in a direction perpendicular to the cartilage surface as shown in FIG. 8. The true ultrasound speed ($v_s$) in the articular cartilage was calculated from the difference in echo times before and after the pre-determined displacement of the ultrasound transducer, i.e., $v_s=2d_s/(t_1-t_2)$.

The thickness (h) of the articular cartilage was determined from the true ultrasound speed ($v_s$) and the initial ultrasound echo time ($t_1$), i.e., $h=v_s t_1/2$. The measured thickness of the articular cartilage was then compared with that obtained by using a direct microscopic optical method. Jurvelin, J. S., et al., *Comparison of Optical, Needle Probe and Ultrasonic Techniques for the Measurement of Articular Cartilage Thickness,* 3 Biomechanics 231–35 (1995).

In this validation test, a pre-determined displacement of 50 μm with a ramping speed of 10 μm/sec was used, and the echo time was measured when the relaxation was finished (i.e., when the load relaxation rate was less than 0.1 g/min). The tests were conducted in a saline solution container at room temperature to prevent dehydration of the specimen during measurement.

Indentation Stiffness Measurement

The ultrasound transducer (3 mm in diameter) was used as the indenter tip for an indentation test for articular cartilage. After an initial contact between the ultrasonic indenter tip and the cartilage surface was achieved and equilibrated under a preload of 0.5 g, eight consecutive indentation displacements (20 μm per step with a ramping speed of 10 μm/sec) were applied to the cartilage surface. Each indentation test consisted of a ramping phase for 2 seconds followed by a complete force-relaxation phase. The reaction force during each indentation test was measured by a low-capacity, 250-gram load cell, which was obtained from SENSOTEC (Ohio), connected to the ultrasound transducer. During each indentation step, a completion of the relaxation phase was determined when the force relaxation rate was less than 0.1 g/min. The time, the reaction-force, and the displacement data during the indentation test were collected, at a sampling rate of 1 Hz, using a data acquisition system which is commercialized, under the designation "DAQ-AI-16XE-50, by National Instrument Corporation (Austin, Tex.).

A thickness for the articular cartilage was determined obtained, using the in situ calibration method mentioned above, during the first three indentation steps (total displacement =60 μm). As FIG. 9 indicates, the equilibrium force-percent strain curve was obtained, and the indentation stiffness (g/percent strain) was measured from the linear region of the curve. In the linear curve range (line, usually over 5%), the indentation stiffness (slope, unit: g/percent strain) was measured. A complete set of indentation experiment took about three hours for each specimen.

Proteoglycan-depleted Osteoarthritis-like Cartilage Specimen

In order to test our ultrasonic indentation protocol for OA-like cartilage specimen found in clinical situations, we extracted proteoglycan from articular cartilage using an enzymatic digestion method. Twenty osteochondral plugs (ten for the validation of the in situ calibration technique and ten for the indentation test) were treated with trypsin (1 mg/ml) in 0.15 M NaCl and 0.05 M Na phosphate for 20 minutes at 37° C. After trypsin treatment, specimens were rinsed with a phosphate buffered saline solution for 1 hour at room temperature and tested immediately.

After the thickness measurements and indentation tests were performed, the amount of PG present in each cartilage specimen was measured for ten normal cartilage specimens and ten PG-depleted cartilage specimens. Approximately the same amount of full thickness cartilage sample was excised from the testing site of each osteochondral plug. After carefully blotting the surface water on the specimen using facial tissue, the wet-weight of the cartilage specimen was measured on an analytical balance. After the cartilage sample was minced with a surgical blade, PG was then extracted with PG-extraction solution (4 M guanidine HCl, 0.5 M Tris, 1 mM EDTA, pH 8.0, 10 mg/ml dithiothreitol) for 4 hrs and then 30 mg/ml iodoacetic acid was added to the PG-extraction solution. The amount of PG in each specimen was then measured using 1,9-dimethylmethylene blue binding assay, and normalized with respect to the wet weight of each sample.

Histological evaluations of the normal cartilage and the enzymatically treated (PG-depleted) cartilage were also performed using toluidine blue staining to qualitatively evaluate the distribution of GAG molecules in the specimen.

Statistical Analysis

Statistical analysis was performed using a Student t-test to determine the effect of the enzymatic treatment (PG-depleted AC) on the indentation stiffness of the AC, the ultrasound speed, and quantity of PG in the AC. Statistical significance was set at $p<0.05$.

Results

True Ultrasound Speed and Cartilage Thickness

Figure 10:
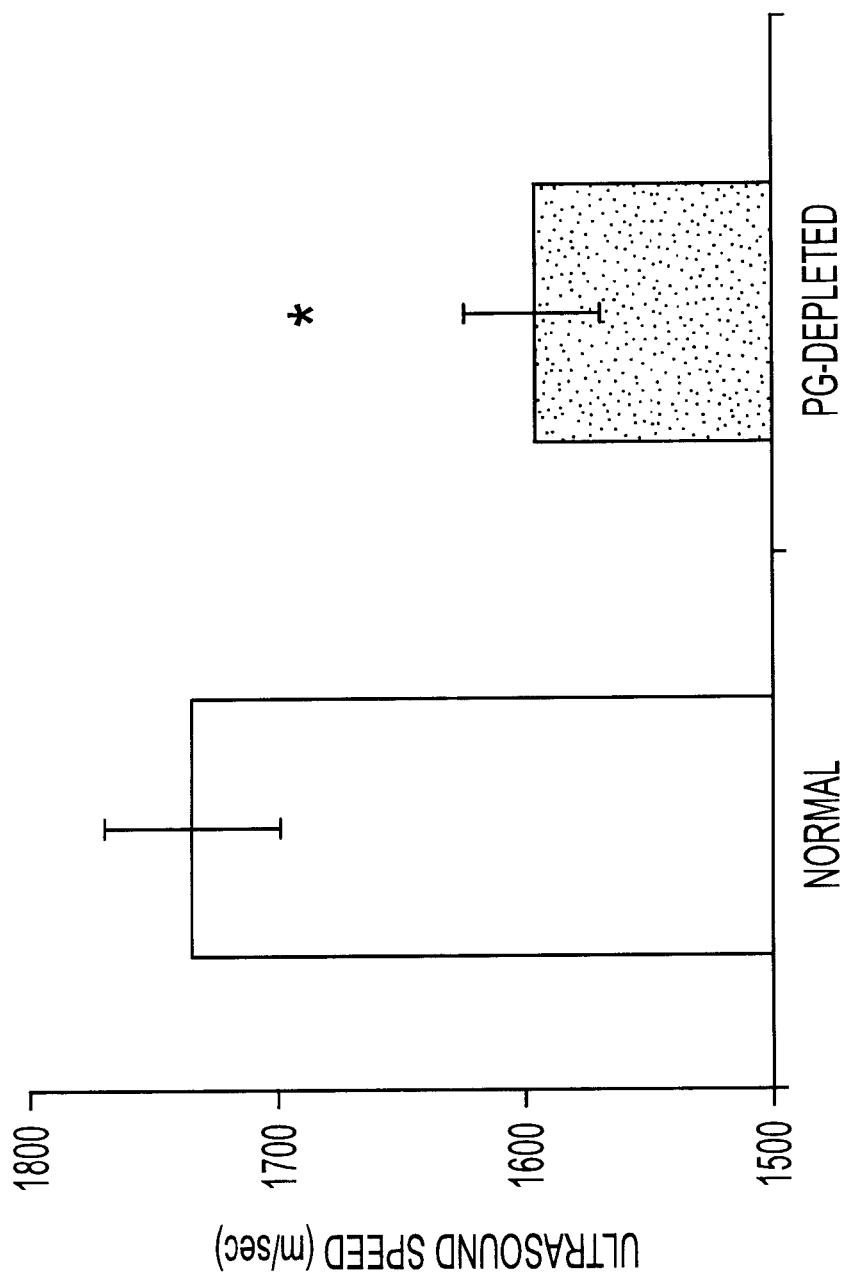
FIG. 10 shows the true ultrasound speed measured with the in situ method according to the invention.

Using the in situ calibration method, the true ultrasound speed was first determined and the thickness of cartilage specimen was then estimated from the echo times and the measured true ultrasound speed for the normal and the PG-depleted cartilage specimens. FIG. 10 shows the true ultrasound speed measured by the in situ calibration method.

The ultrasound speeds in articular cartilage were 1736±45 m/sec for the normal cartilage specimens (n=10), and 1593±30 m/sec for the PG-depleted OA-like cartilage specimens (n=10). The difference between the normal and the PG-depleted cartilage specimens was statistically significant with $p<0.05$.

Figure 11A:
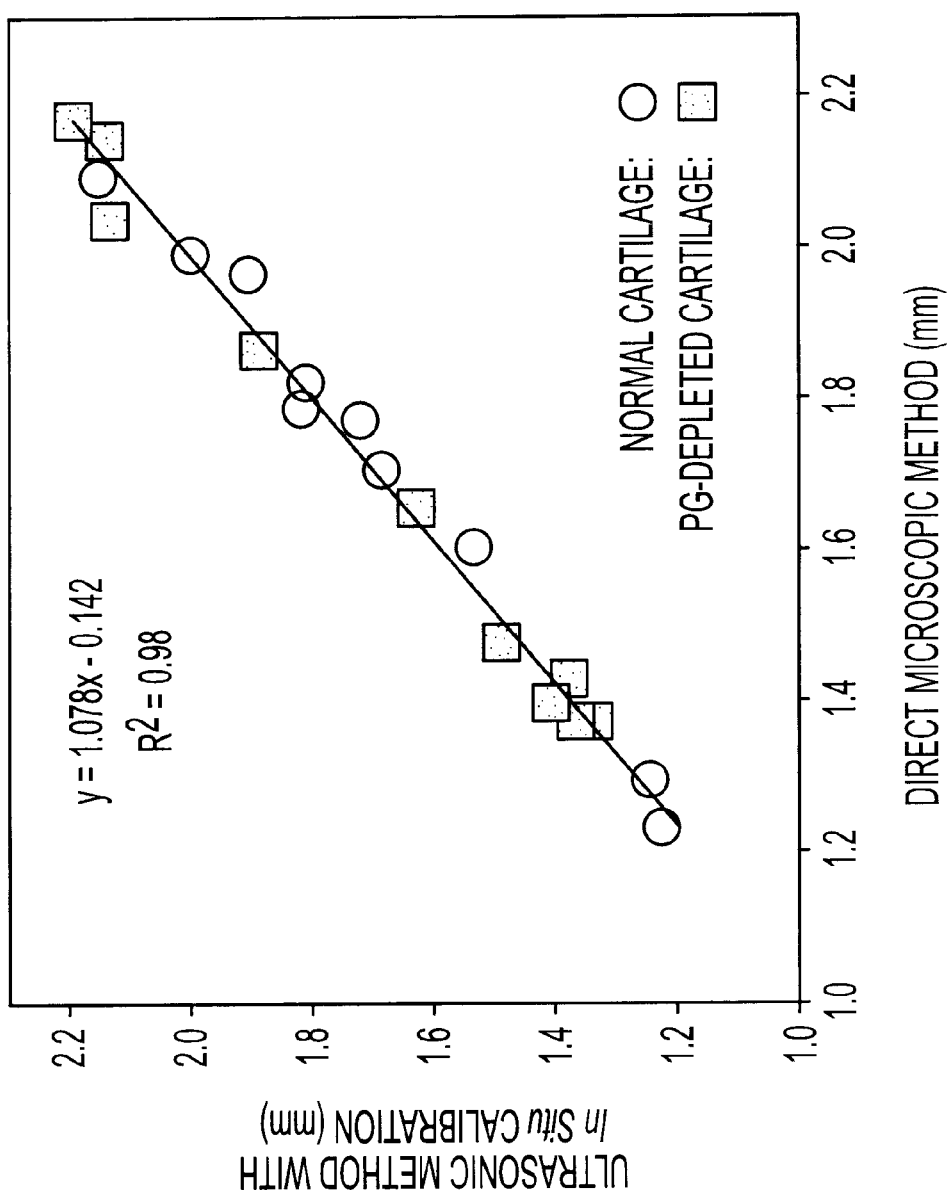
FIG. 11a is a graph demonstrating the correlation between the cartilage thickness measurement with the ultrasonic method with in situ calibration vs. the direct microscopic method.
Figure 11B:
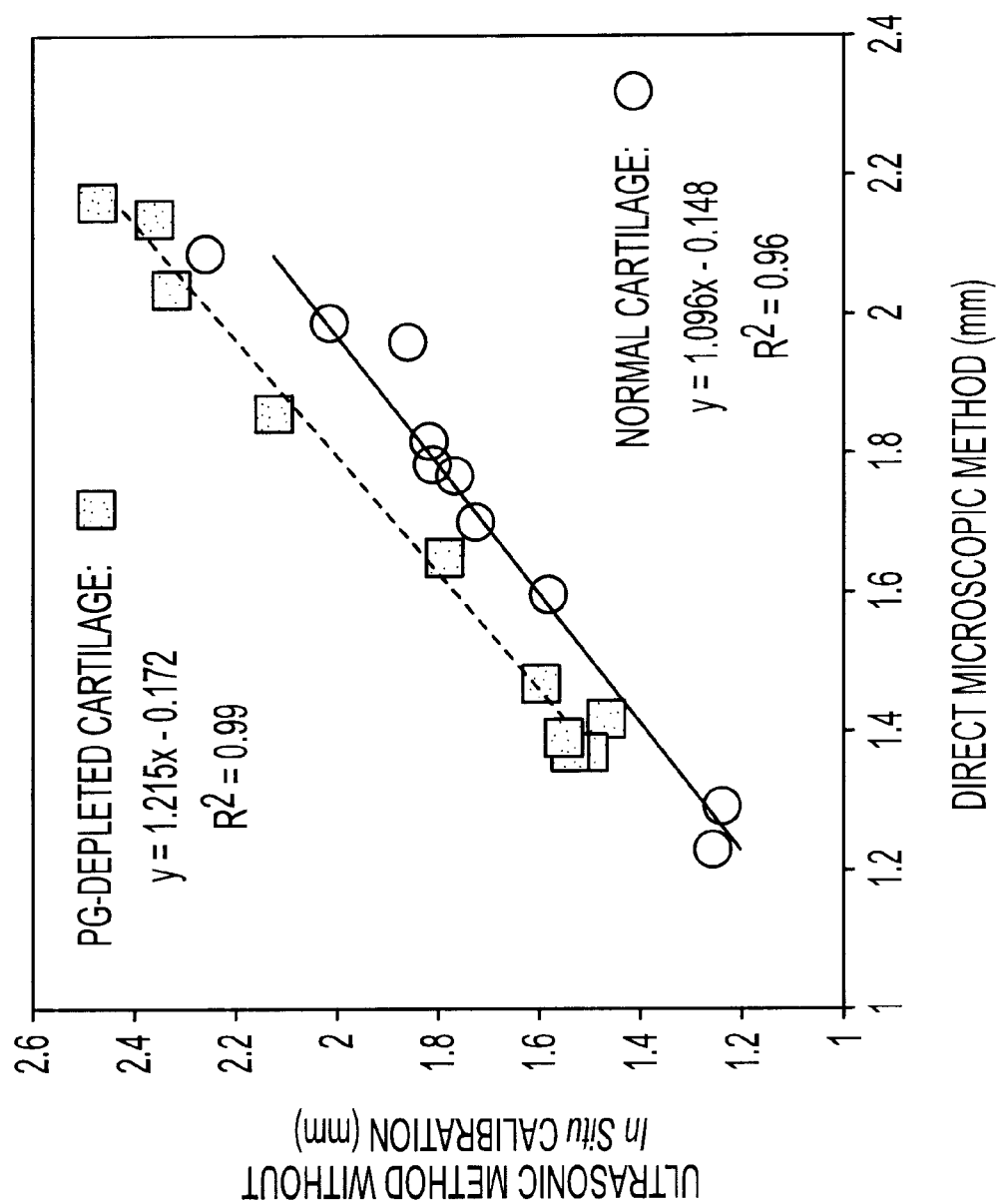
FIG. 11b is a graph demonstrating the correlation between the cartilage thickness measurement with the ultrasonic method without in situ calibration vs. the direct microscopic method.

FIGS. 11a and 11b show the correlations between the cartilage thickness measurement obtained with the ultrasonic transducer with or without the in situ calibration method and that obtained with the direct microscopic method. When the in situ calibration method was used (FIG. 11a), the correlation between the ultrasonic method and the direct microscopic method was excellent with a slope of 1.08 ($R^2=0.98$) regardless of tissue conditions (normal or PG-depleted). The cartilage thickness measured with the ultrasonic transducer was slightly smaller than that directly measured under an optical microscope, as represented by the negative y-axis intercept in the regression equation, y=1.078x−0.1424. This was due to the pre-deformation of cartilage specimen under the application of 0.5 g during the pre-loading condition before the initiation of the ultrasonic thickness measurement.

To investigate the effect of the error in the estimated ultrasound speed on the cartilage thickness measurement, the cartilage thickness was also estimated from an approximated ultrasound speed of 1760 m/sec and the measured echo times, and compared with that obtained using the direct microscopic method (FIG. 11b). It was found that the use of an approximated ultrasound speed produced an excellent prediction of the tissue thickness for normal cartilage with y=1.096x−0.148 ($R^2=0.96$). The PG-depleted cartilage, however, showed a poor correlation with y=1.215x−0.172

($R^2$=0.99), indicating that an accurate estimation of ultrasound speed is important in determining the cartilage thickness.

Indentation Stiffness and PG Analysis of Cartilage

Figure 9:
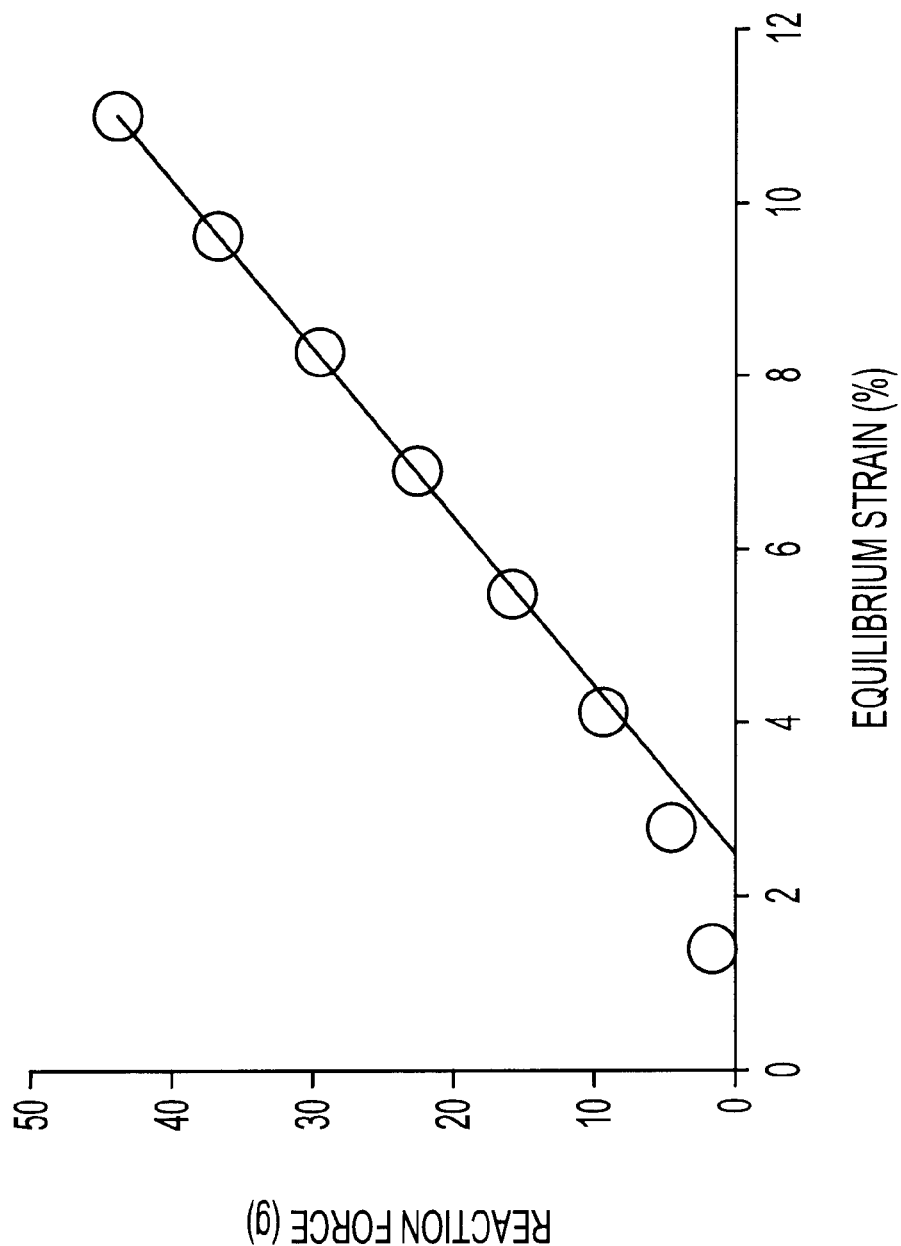
FIG. 9 shows a typical example of the equilibrium force-strain behavior of bovine patella groove in a continuous indentation test.
Figure 12:
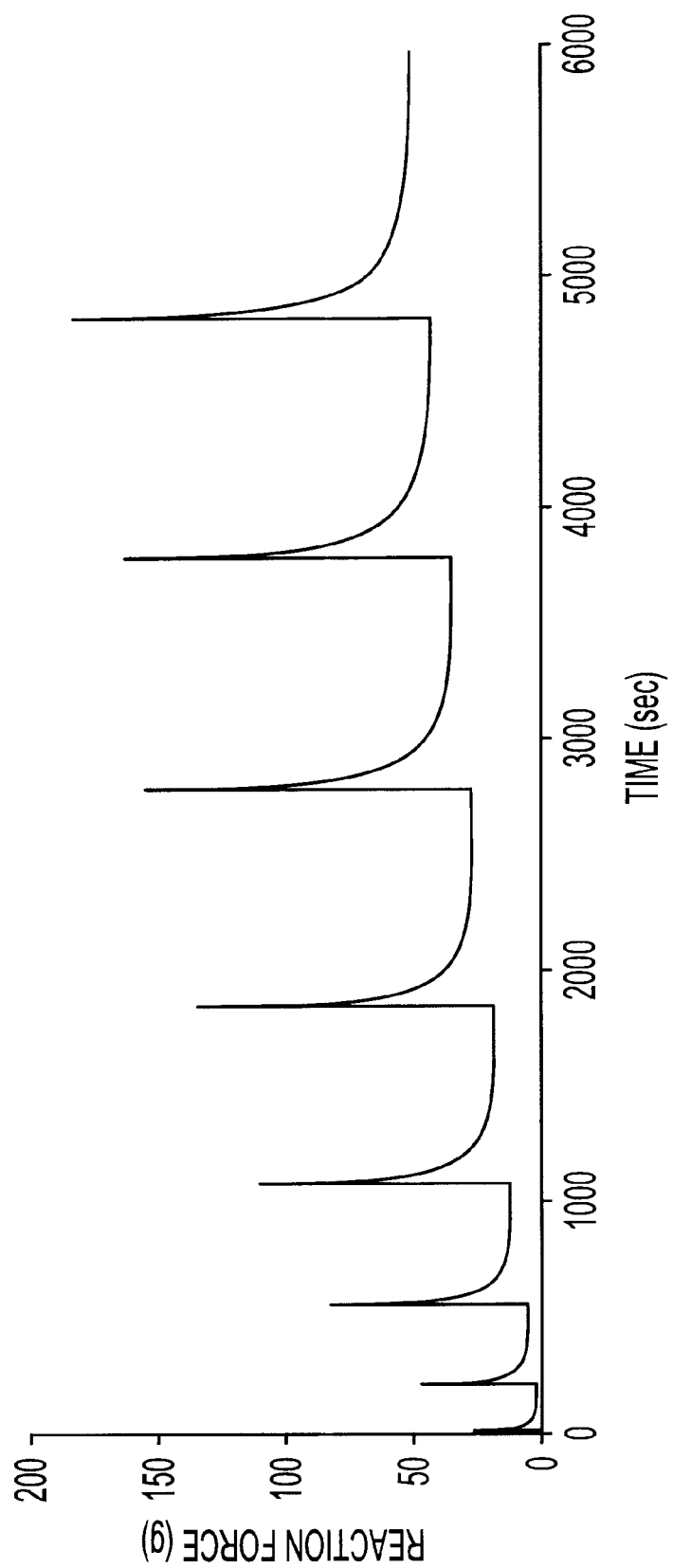
FIG. 12 shows a typical reaction force-time curve taken on a series of eight consecutive indentation stress-relaxation tests.

A typical reaction force-time curve and a typical equilibrium force-percent strain curve for the eight consecutive relaxation tests are shown in FIGS. 12 and 9, respectively. It was found that the linear region of the equilibrium force-percent strain curve usually occurred around 5–8 percent strain, from which the indentation stiffness was evaluated.

Figure 13:
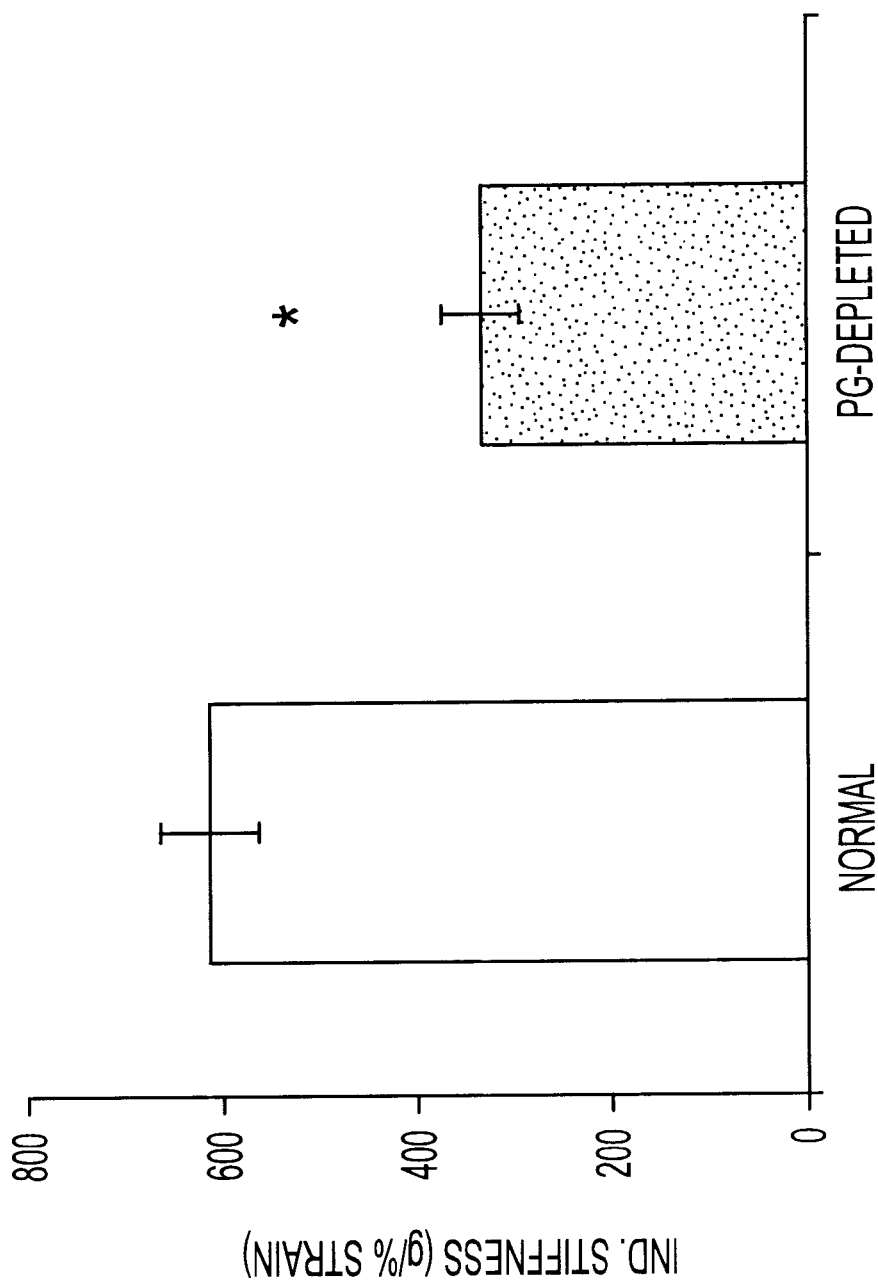
FIG. 13 compares the average indentation stiffness of normal and PG-depleted cartilage specimens.
Figure 14:
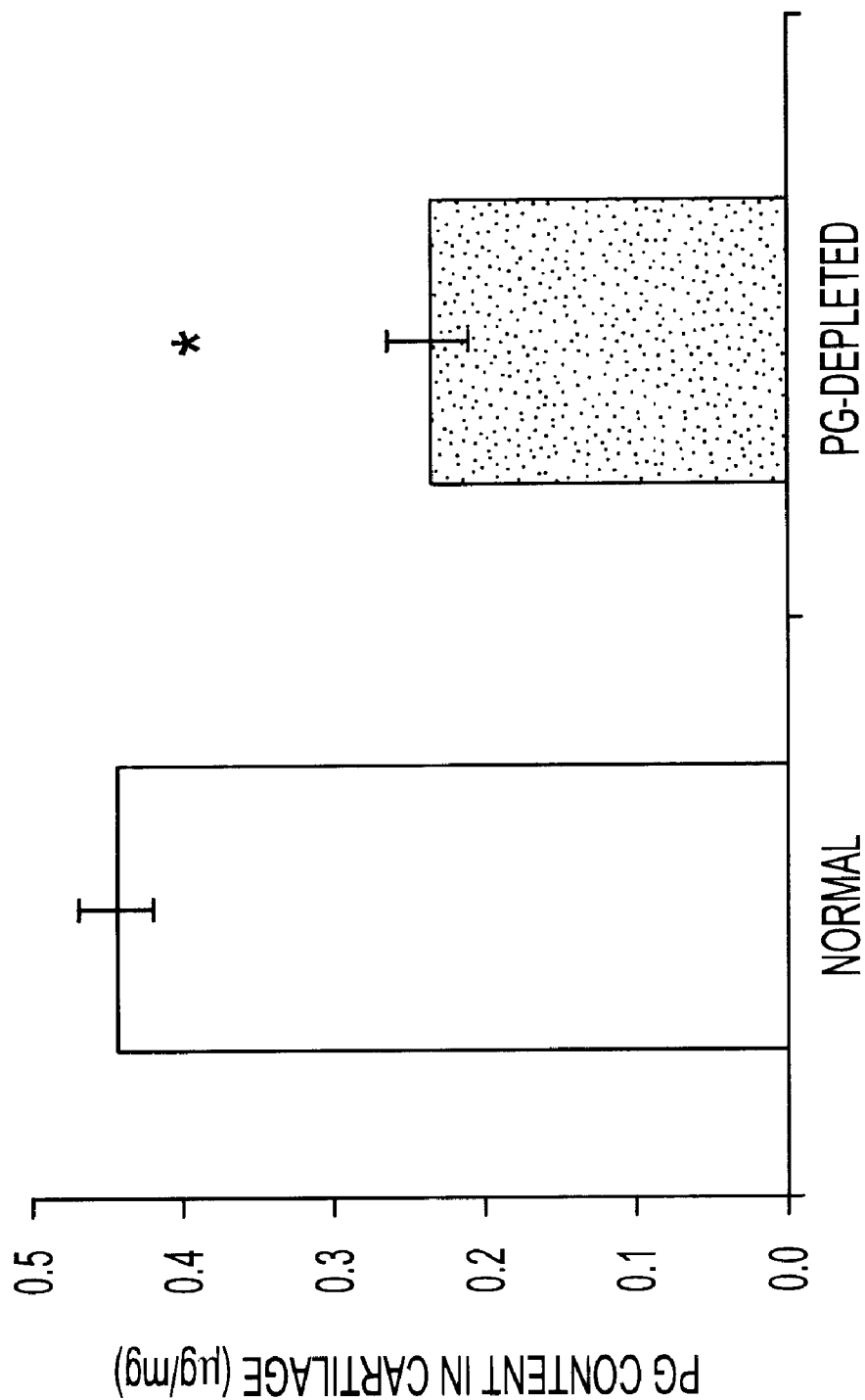
FIG. 14 compares the normalized PG content in the normal and the PG-depleted cartilage specimens.

FIG. 13 shows the average indentation stiffness of normal and PG-depleted cartilage specimens. A significant decrease in the indentation stiffness was found for PG-depleted cartilage specimen as compared to normal cartilage; the indentation stiffness of PG-depleted cartilage was 330±31 g/percent strain (mean ±SD, n=10), whereas that of normal cartilage was 637±54 g/percent strain (mean ±SD, n=10). Accordingly, the quantitative PG measurement, FIG. 14, revealed that the trypsin treated cartilage specimens had a significantly decreased PG content (0.24±0.03 (µg/mg), mean ±SD, n=10), as compared to the normal cartilage (0.45±0.03 (µg/mg), mean ±SD, n=10).

Figure 15:
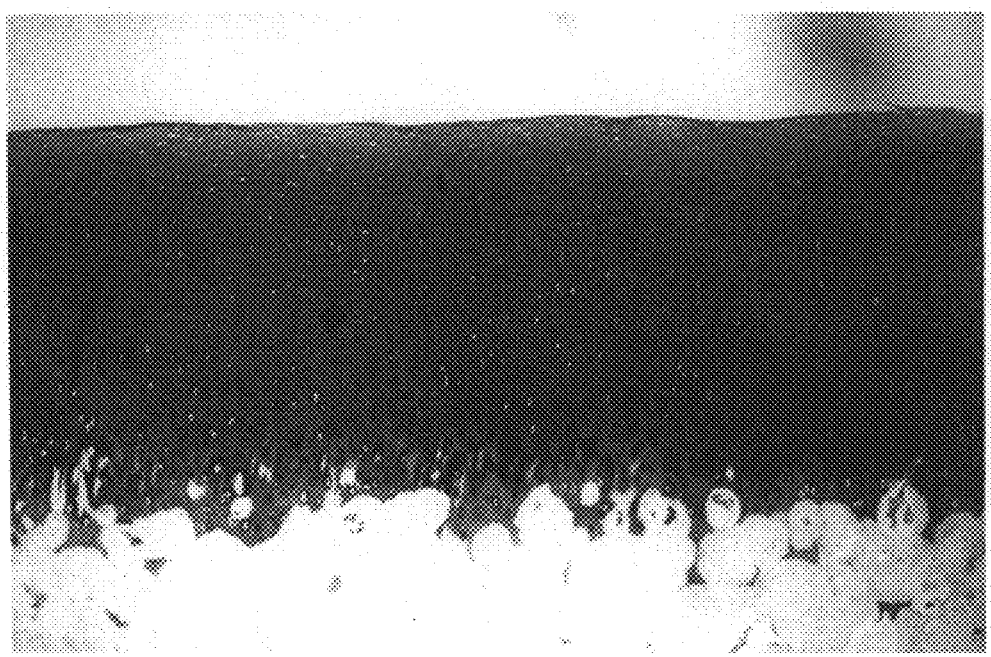
FIG. 15 shows a normal bovine cartilage bone plug stained with toluidine blue.
Figure 16:
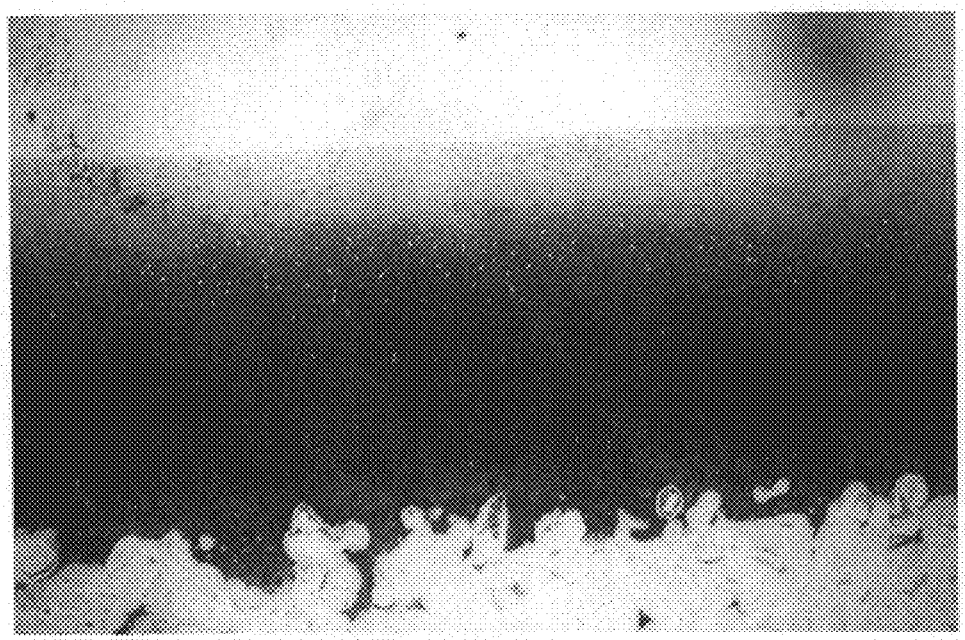
FIG. 16 shows an enzymatically treated cartilage bone plug stained with toluidine blue.

Histologically, the normal cartilage specimen (FIG. 15) demonstrates a relatively uniform toluidine blue staining from the surface to the tidemark of articular cartilage, representing a uniform distribution of PG molecules in the tissue. In contrast, the trypsin treated cartilage (FIG. 16) demonstrates a significant loss of the staining, in the top 25% region of the cartilage matrix. During the trypsin treatment for 20 minutes, the enzyme penetrated downward one-dimensionally into the cartilage matrix, resulting in a significant depletion of PG molecules highly localized over the superficial zone of the cartilage specimen. It was found that such superficial tissue damage was well represented by a significant decrease in the indentation stiffness by 48% (from 637 g/percent strain to 337 g/percent strain).

As demonstrated, an in situ calibration method was utilized, using an ultrasonic transducer, to predict accurately the true sound speed in articular cartilage. With such a prediction, the thickness of articular cartilage was determined and, hence, the intrinsic indentation stiffness of the tissue in a non-destructive manner. The above-discussed data indicated that the accuracy of cartilage-thickness measurement with an ultrasound transducer is strongly dependent on the accurate estimation of the true ultrasound speed in the tissue. It was also demonstrated that the ultrasound speed in articular cartilage is dependent on the tissue conditions (normal or pathological), which is consistent with a previous study. Myers, et al., *Experimental Assessment By High Frequency Ultrasound of Articular Cartilage Thickness and Osteoarthritic Changes*, 22 J. Rheumatology 109–116 (1995). Myers, et al. previously reported that the speed of sound was 1658±185 m/sec and 1581±148 m/sec for normal and OA human femoral cartilage specimens, respectively.

When a material is isotropic and homogenous, the sound speed in the material can be mathematically written in terms of the elastic modulus and the density of the material as follow:

$$v = \sqrt{\frac{E}{\rho}}$$

where E is the elastic modulus and p is the density. While articular cartilage is not isotropic and homogeneous, the ultrasound speed in articular cartilage is still expected to represent the elastic properties and the density of cartilage. Therefore, the ultrasound speed in the tissue is sensitive to the changes in the molecular constituents of the tissue, such as water content, proteoglycan content, collagen content and their crosslinks. It has been found that PG content can significantly affect both the hydraulic permeability and the elastic properties of articular cartilage. A decrease in the amount of PG present in OA-like cartilage results in an increase in porosity and water content of the tissue matrix, thus causing a decrease in the compressive elastic modulus. This is well demonstrated in the present study that the PG-depleted OA-like cartilage specimens have a lower ultrasound speed along with a decreased indentation stiffness, as compared to the normal cartilage specimens.

Device According to the Invention

Figure 3:
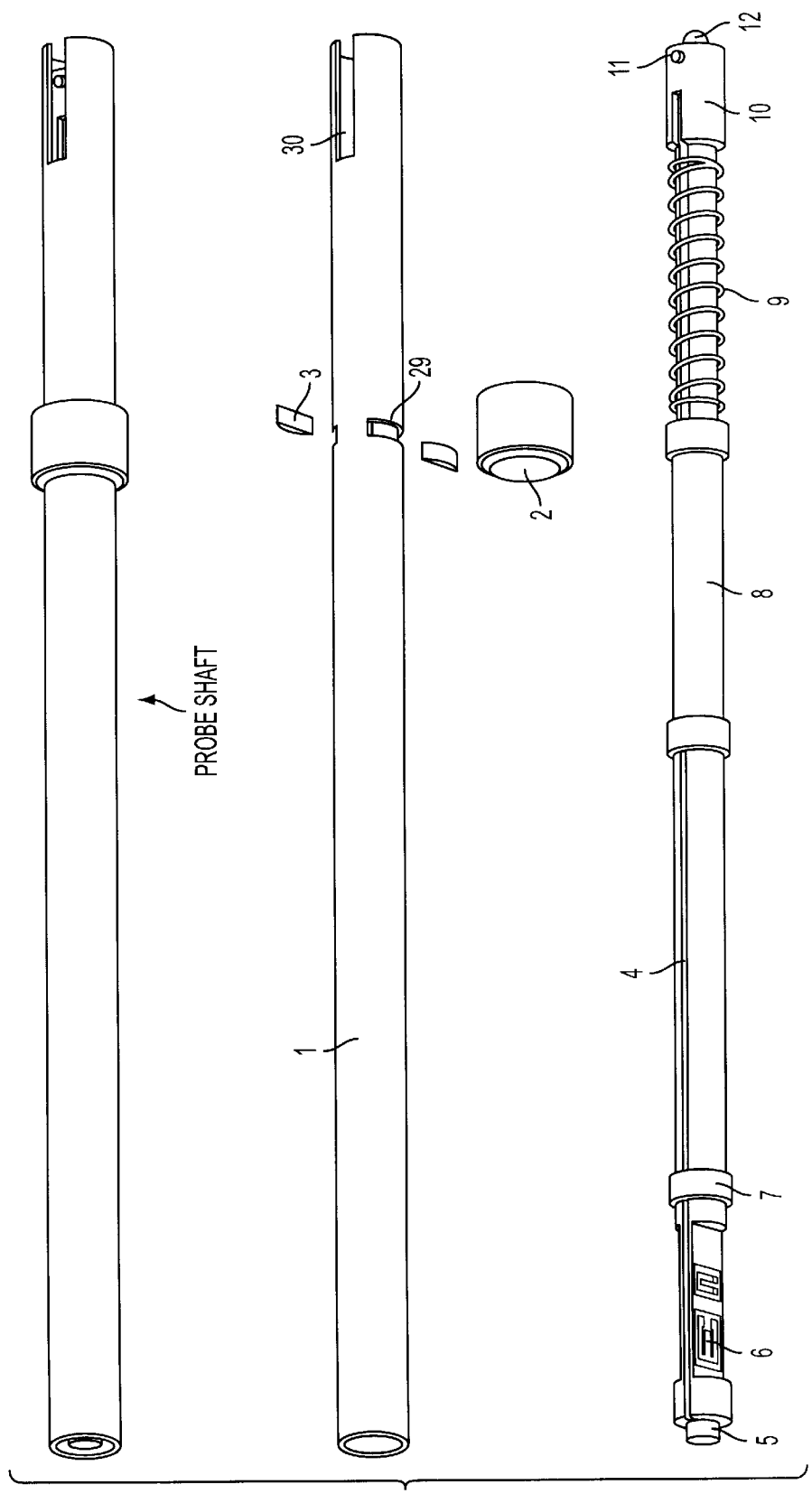
FIG. 3 is a detailed assembly of the probe.
Figure 4:
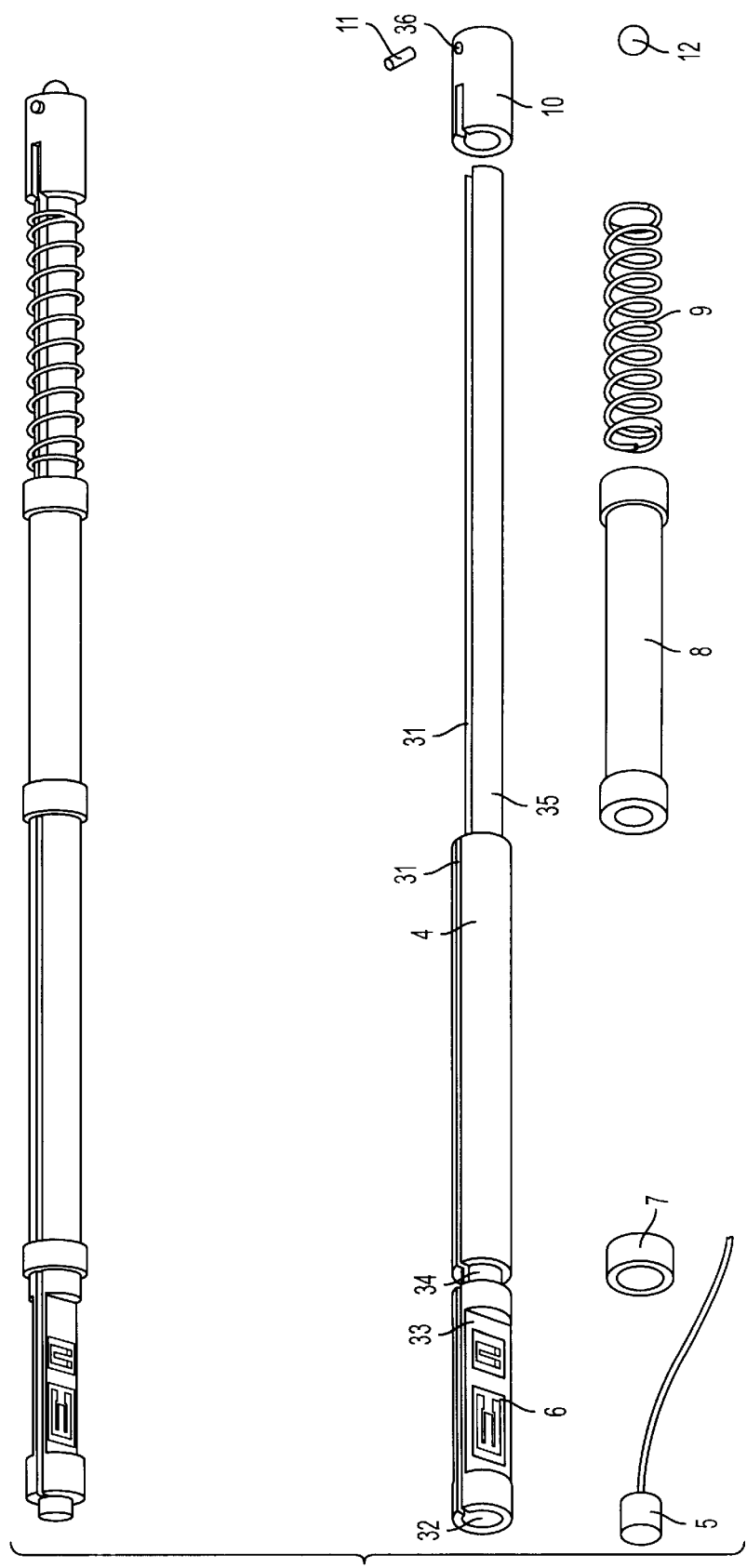
FIG. 4 is another detailed assembly of the probe.

In the indentation-relaxation test for articular cartilage, a constant displacement is applied to the cartilage surface via an indenter tip and the indentation-relaxation force is measured with strain-gauges as a function of time. A constant displacement of the indenter tip is produced in a ramp function by a micro stepper-motor and a miniature micrometer. The relaxation force is measured by a Wheatstone bridge circuit of four strain-gauges with temperature compensators. As shown in FIGS. 3 and 4, a full-bridge configuration (four strain gauges 6) with a longitudinal strain-gauge and a transverse dummy strain-gauge on each side of a flat surface 33 is most popular for axial loads. The output voltage from the full-bridge not only is higher, by approximately one gain factor, but is less nonlinear than for a half-bridge system. This force measurement system has good temperature compensation because strain-gauges are present in all adjacent surfaces 33. To get a stable output, the inventive probe uses a precision differential amplifier chip for acquiring data. Illustrative of the later is an AD524 series sold by Analog Devices (MA).

To make the inventive probe both accurate and easy-to-use, while minimizing human error, a fully automated computer control system preferably is employed. The computer control system is comprised of a displacement control system, for the indenter, which is driven by a micro-stepper-motor, a force measurement system, which is based on a Wheatstone bridge strain-gauge circuit with a temperature compensator, and a cartilage thickness measurement system with a miniature ultrasonic transducer. The ultrasonic transducer, or indenter tip, is fixed at the end of the displacement actuator. The indenter tip of the probe is used to apply a predetermined displacement to the cartilage surface. During this predetermined displacement, which is driven by the micro-stepper-motor, the strain-gauges attached to the displacement actuator measure the relaxation force exerted by the articular cartilage.

Using the displacement control mechanism with the ultrasonic transducer according to the present invention allows the speed of the ultrasound to be calibrated in the articular cartilage in situ. This unique method can be performed by applying a predetermined displacement, via the ultrasonic transducer, in a direction perpendicular to the cartilage surface, thereby avoiding the external calibration procedure of conventional ultrasonic transducers. The sound speed measured by this in situ calibration method is critically important to estimating accurately the thickness of articular cartilage.

The probing part can be readily placed into a conventional arthroscopic portal during an arthroscopic procedure. The measured data are collected by a real-time data acquisition system installed on a portable notebook computer, which is connected directly to the probe via a connector port of the probe handle. The reaction force data and the cartilage-thickness data then are analyzed automatically by the computer program, to estimate the mechanical (static and dynamic) properties of the articular cartilage. All of the testing and data analysis procedures are controlled automatically by the computer program, with a graphic user interface to provide user-friendly operation in clinical settings.

Figure 1:
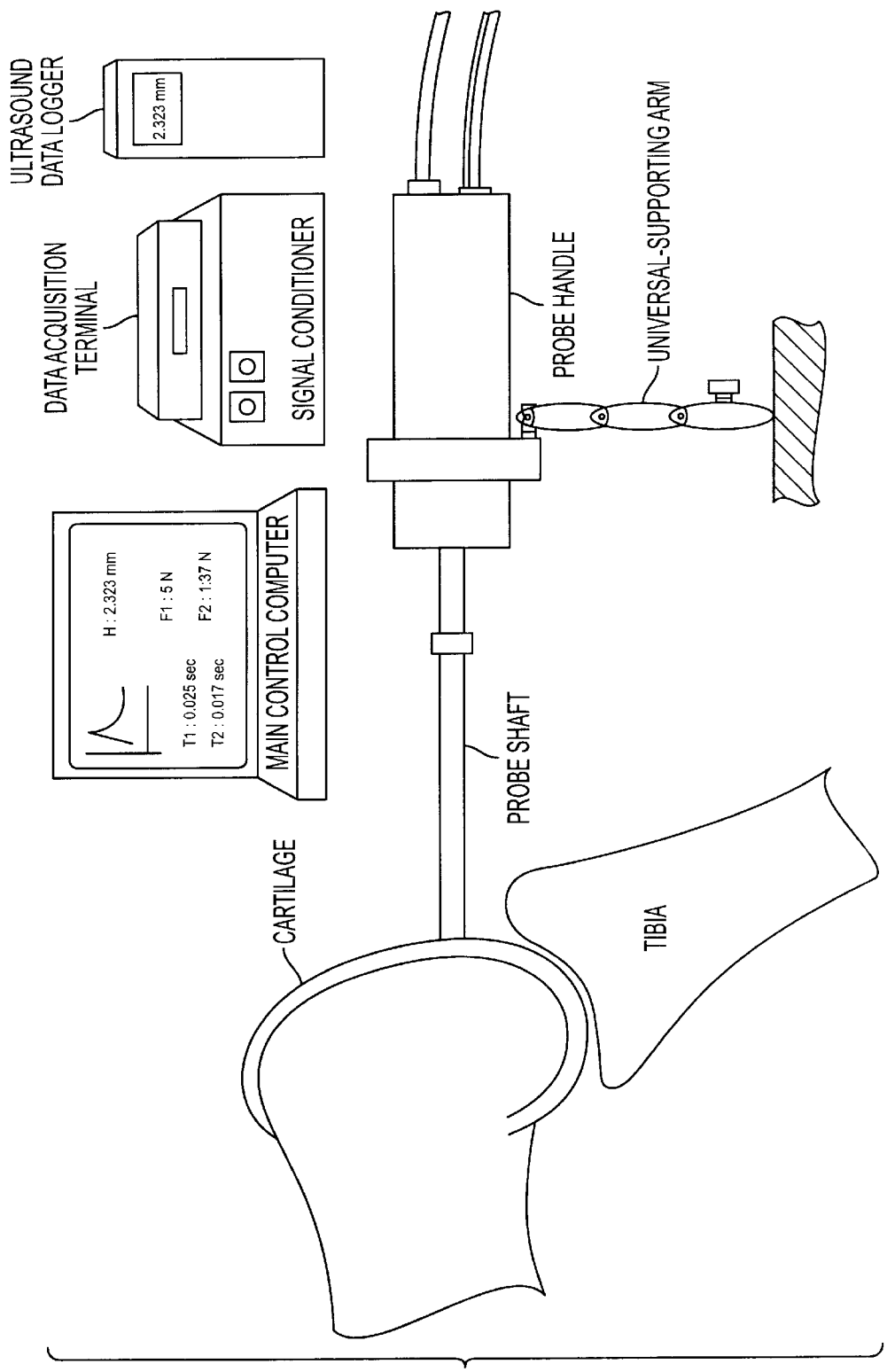
FIG. 1 is an overall schematic view of the measurement system.

FIG. 1 provides a schematic view of the overall measurement system. The arthroscopic mechanical probe is controlled by a portable notebook computer, which is interfaced with a signal conditioner, a data acquisition system, and an ultrasonic measurement device. The universal-supporting arm attached to the probe allows for flexibility, by virtue of the system's easy positioning as well as rigid fixation of the probe to orthopedic surgeons.

Figure 2:
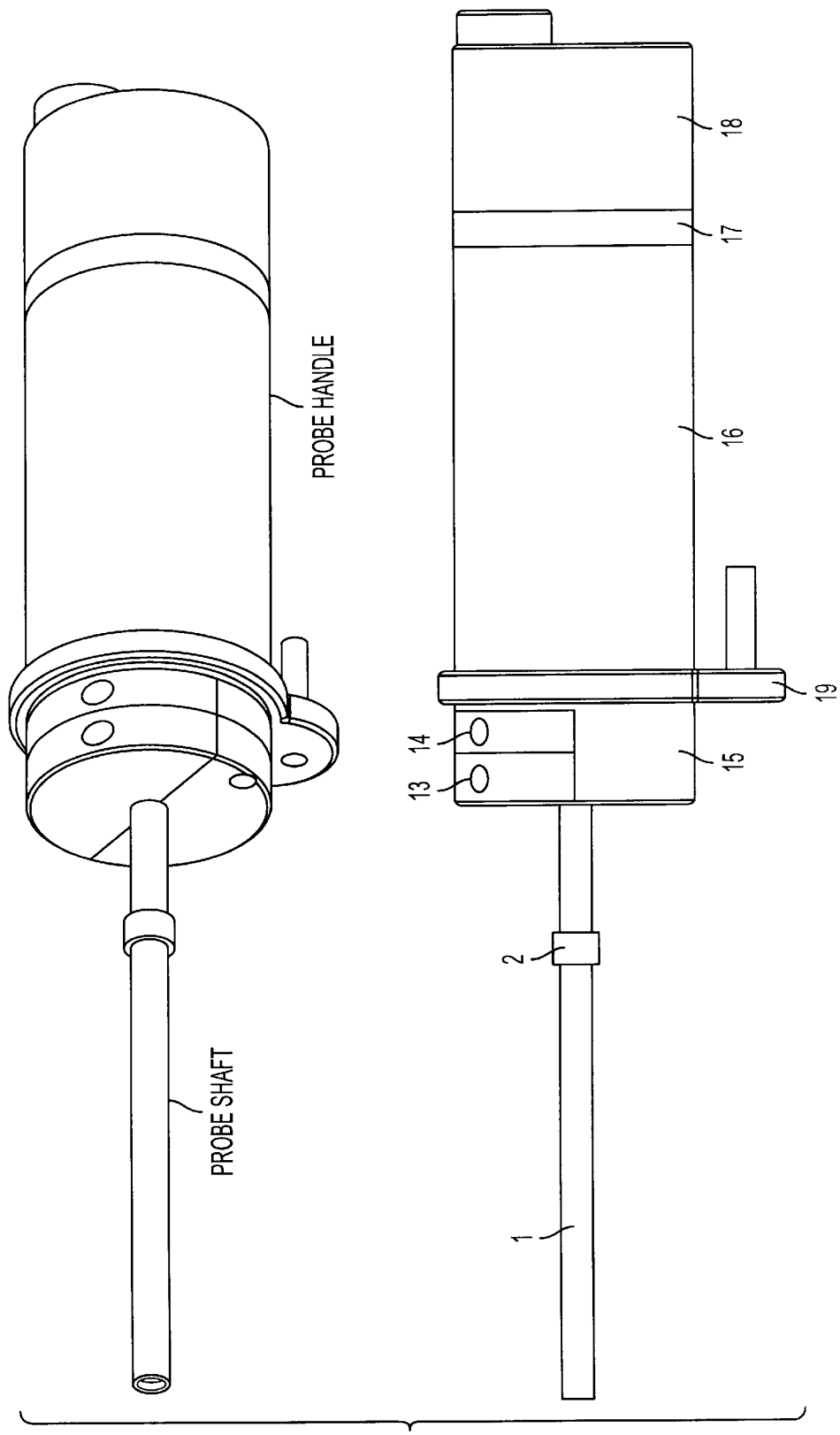
FIG. 2 is a three-dimensional schematic of the probe.

FIG. 2a is a three-dimensional schematic of the probe in a perspective view, which consists of the probe shaft and the probe handle. FIG. 2b shows an assembled version of the probe of the present invention.

FIGS. 3 through 4 show a detailed assembly of a probe shaft according to the present invention. The housing cylinder 1, preferably, is made of 316 L stainless steel and, preferably, has an outer diameter of 0.25 inches and a length of 5 inches. Slot 29 on the housing cylinder 1 is adapted for the insertion of the spring retaining pin 3. The Teflon spring holder retaining ring 2 is press-fitted to firmly fix the spring retaining pin 3 on the housing cylinder 1.

The electric wires for the ultrasonic transducer 5, preferably, model number XMS-310 by Parametrics (Waltham, Md.) and the strain-gauges 6 run through slit 31 and project from slit 30. Slit 30, preferably, has a width of 0.08 inches and a length of 0.5 inches. The ultrasonic transducer 5 is placed into hold 32 and two strain-gauges 6 are attached on each side of a flat surface 33.

The linear displacement actuator 4, preferably, is made of 316 L stainless steel. Teflon sliding guides 7, 8 are placed on surfaces 34, 35 of the linear displacement actuator 4 to provide smooth traveling for the linear displacement actuator 4 in the housing cylinder 1. The positioning spring 9, which is, preferably, made of stainless steel, is placed along the linear displacement actuator 4. The positioning spring 9 is butted distally by the spring retaining pin 3, which is fixed on the housing cylinder 1, and butted proximally by the spring retaining cap 10, which is fixed at the end of the housing cylinder 1. This provides the axial retraction force to the linear displacement actuator 4.

The anti-rotational pin 11, preferably, is made of Teflon and has a diameter of 0.05 inches, fits into hole 36 of the spring retaining cap 10, protrudes, preferably, by 0.03125 inches, and slides along slit 30 of the housing cylinder 1. This ensures accurate axial traveling of the linear actuator 4 without any rotation. The axial traveling of the linear displacement actuator 4 is created by an axial displacement of the micrometer head loading shaft 37.

A stainless steel ball 12 is used between the proximal face of the spring retaining cap 10 and the micrometer head loading shaft 37 to decrease the friction force between the spring retaining cap 10 and the micrometer head loading shaft 37.

Figure 5:
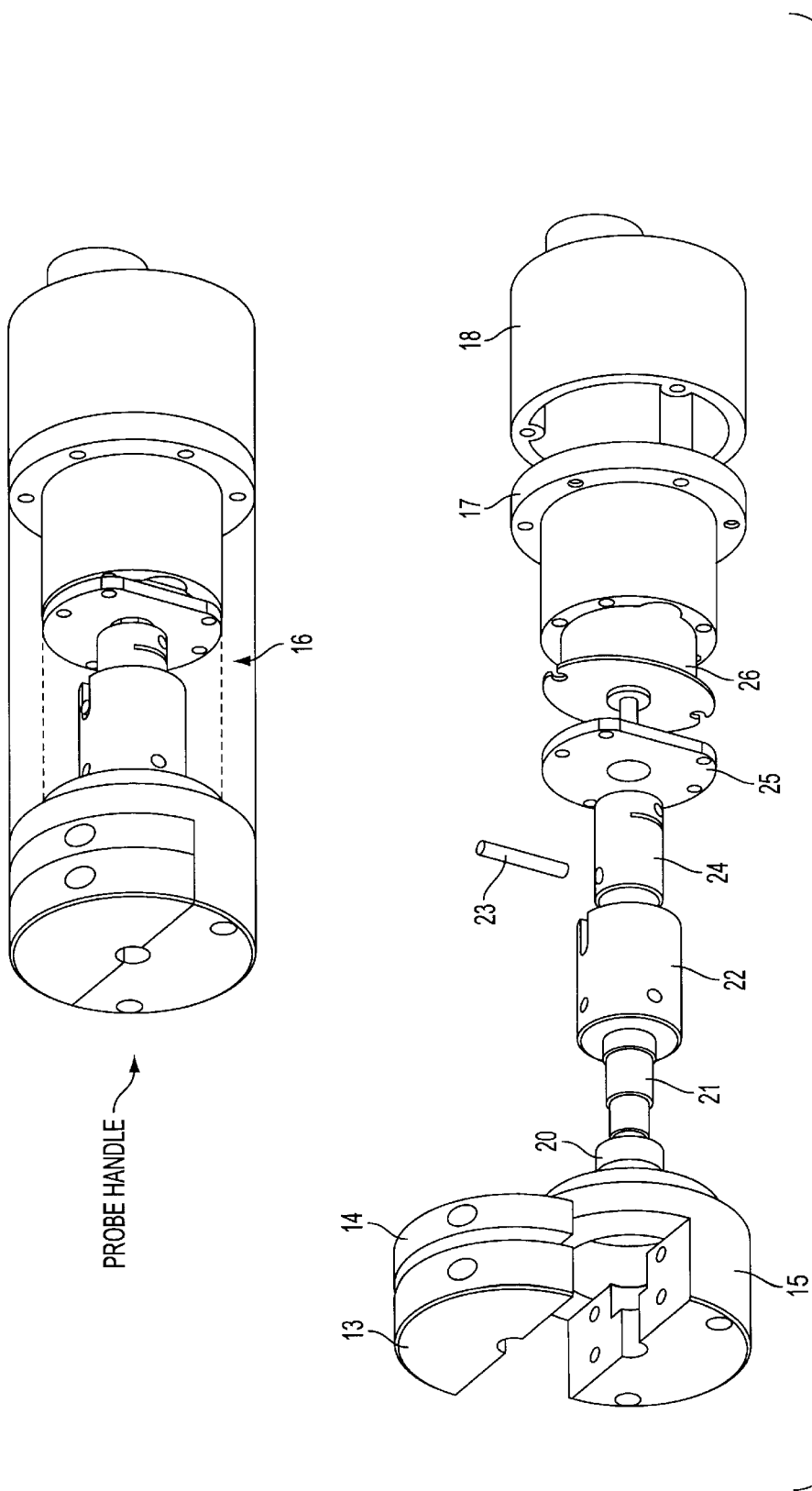
FIG. 5 is a detailed assembly of the probe handle.

FIG. 5a shows an assembled probe handle separated from the probe shaft. A detailed assembly of the probe handle is shown in FIG. 5b.

Figure 6:
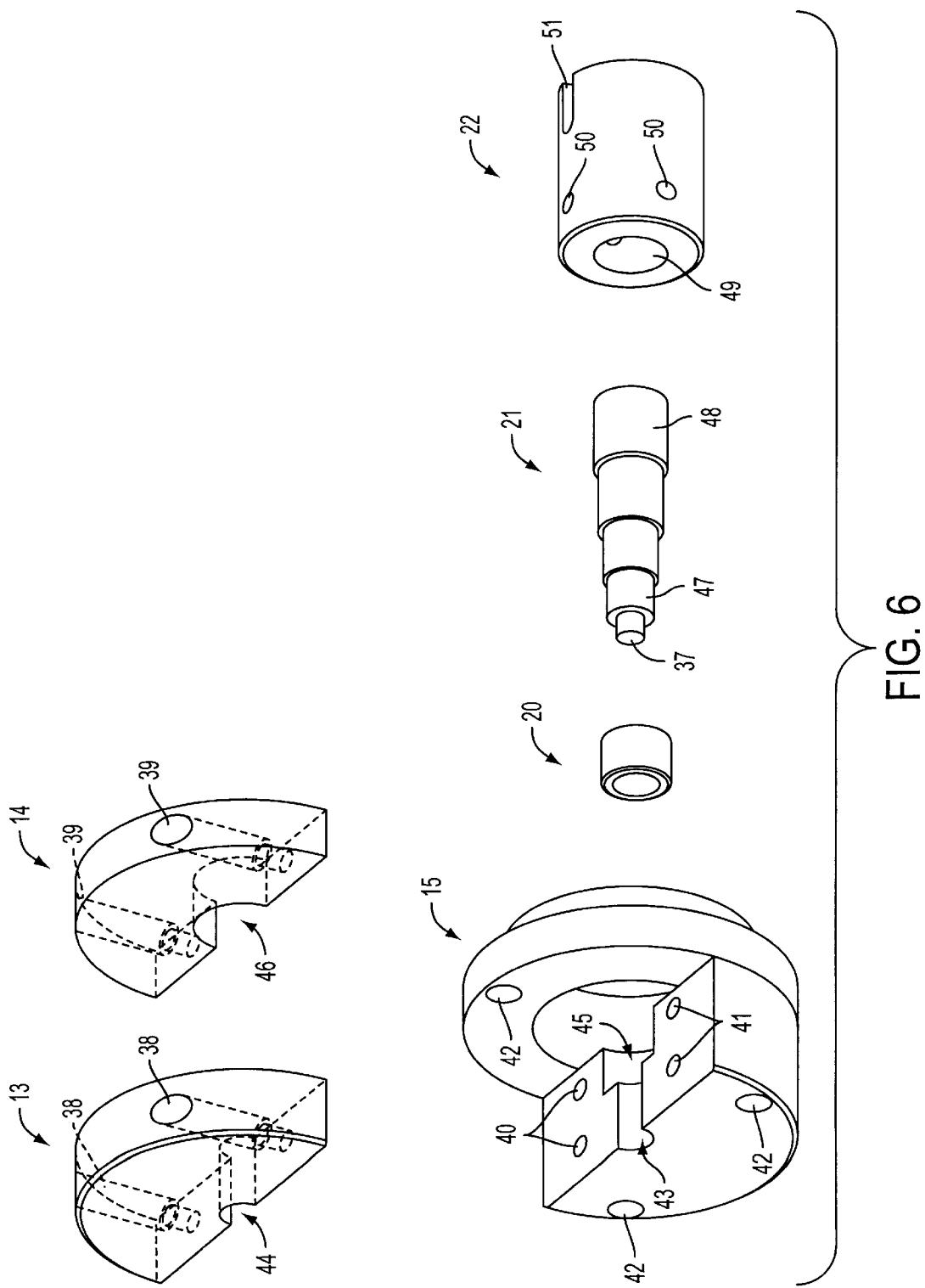
FIGS. 6 and 7 show an even more detailed assembly of the probe handle.
Figure 7:
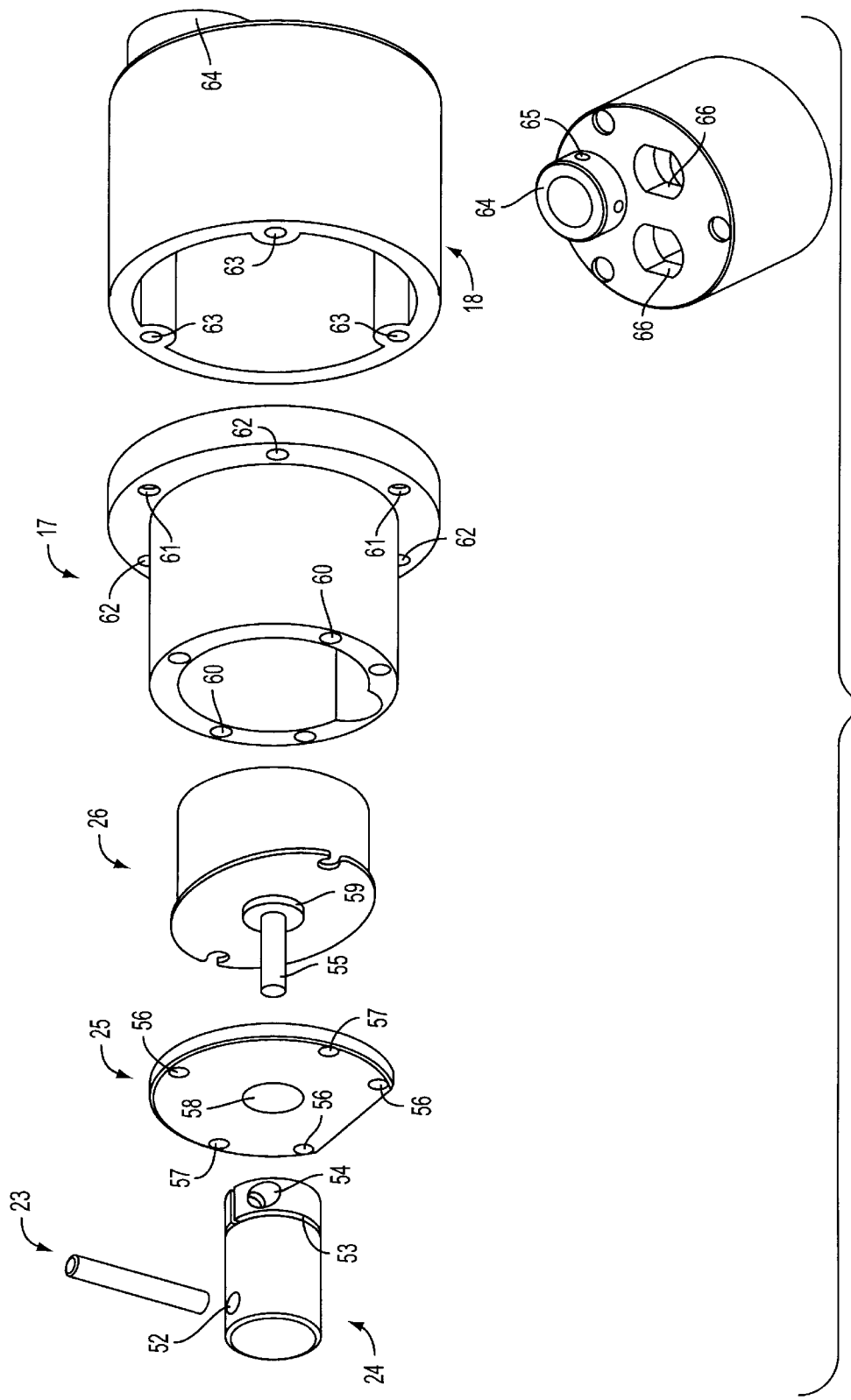

As shown in FIGS. 6 and 7, the housing cylinder holder 13, micrometer head holder 14, and the housing cylinder and micrometer head holder 15, are easily assembled, preferably, with #4–40 screws inserted through screw holes 38, 39, 40 and 41. The handle 16 is screwed into the housing cylinder and micrometer head holder 15 via holes 42. The housing cylinder 1 is firmly placed into a hole, and firmly held therein, formed by a half-round slot 43 on the housing cylinder holder 13 and an opposing half-round slot 44 on the housing cylinder and micrometer head holder 15. Once the housing cylinder 1 is placed in the hole, the housing cylinder holder 13 is secured to the housing cylinder and micrometer head holder 15.

The micrometer head 21, illustrated by MITUTOYO No. 148-104, is rigidly connected to the housing cylinder and micrometer head holder 15 and the micrometer head connector 22. The clamping ring for the micrometer 20 is placed in the hole resulting from the joining of a half-round slot 45 of the housing cylinder and micrometer head holder 15 and a half-round slot 46 of the micrometer head holder 14. This clamping ring 20 firmly holds area 47 and sets the alignment of the micrometer head 21. Micrometer head handle 48 is fitted into the hole of connector 49 and, preferably, is fixed with #2–26 set screws through threaded holes 50.

Slit 51, which, preferably, has a length of 0.3 inches and a width of 0.125 inches, is designed to connect the stepper-motor shaft connector 24 to the rotational pin 23. The 24V rotary stepper-motor 26, illustrated by HIS No. 26440-24; having a hold torque of 1.6 oz-in, an inertia of 1.2 g-cm, and an accuracy of 7.5° per pulse, is held in place by the stepper-motor alignment plate 25 and the stepper-motor holder 17. The rotational pin 23, preferably, is a dowel pin having a diameter of 0.125 inches and a length of 0.7 inches and is firmly fitted into hole 52 of the stepper-motor shaft connector 24. Slit 53 and screw hole 54 are designed to retain the rotary stepper-motor shaft 55. The stepper-motor alignment plate 25 consists of three alignment pin holes 56, two holes 57 for, preferably, #2–56 screws, and one alignment center hold 58. The alignment center hold 58 is press-fitted into the rotary stepper-motor bearing 59.

The stepper-motor holder 17, the handle 16, the stepper-motor alignment plate 25, and the connector and wiring port case 18 are rigidly assembled through screw holes 60, 61, 62, and 63, preferably, via #4–40 screws.

The ultrasound transducer BNC connector is placed into the connector 64 and, preferably, fixed with #2–56 set screws through screw holes 65. Preferably, small size LEMO connectors (EEG 1B), used to connect rotary stepping motor wires and strain-gauge wires, are used to minimize the size of the arthroscopic mechanical probe and are plugged into the holes 66.

Other embodiments of the invention will be apparent to those skilled in the art from consideration of the specification and practice of the invention disclosed herein. It is intended that the specification be considered as exemplary only, with the true scope and spirit of the invention being indicated by the following claims.

What is claimed is:

1. A diagnostic probe for articular cartilage, comprising (A) a probe handle and (B) a probe shaft, fixed to said handle; that comprises a housing cylinder having a proximal end and a distal end, wherein said probe shaft further comprises, from distal to proximal, (i) an ultrasonic transducer attached to the probe shaft at the distal end of said housing cylinder; (ii) a plurality of strain-gauges attached to the probe shaft; and (iii) a linear displacement actuator which is displaceably mounted to said housing cylinder.

2. A diagnostic probe for articular cartilage as claimed in claim 1, further comprising a stepper-motor for actuating said ultrasonic transducer.

3. A diagnostic probe for articular cartilage as claimed in claim 1, wherein said plurality of strain-gauges form a Wheatstone bridge.

4. A diagnostic probe for articular cartilage, comprising (A) a probe handle and (B) a probe shaft, fixed to said handle, that comprises a housing cylinder having a proximal end and a distal end, wherein said probe shaft further comprises, from distal to proximal, (i) an ultrasonic transducer, attached to the probe shaft at the distal end of said housing cylinder, that is adapted to receive an ultrasound echo, (ii) a plurality of strain-gauges attached to the probe shaft, and (iii) a linear displacement actuator that is displaceably mounted to said housing cylinder.

5. A diagnostic probe for articular cartilage as claimed in claim 4, wherein the linear displacement actuator is adapted to provide at least one predetermined displacement of the transducer.

6. A diagnostic probe for articular cartilage as claimed in claim 5, wherein the transducer is adapted to measure an ultrasound echo time.

7. A diagnostic probe for articular cartilage as claimed in claim 6, wherein the probe is further adapted to determine the thickness of articular cartilage by comparing a plurality of measured ultrasound echo times.

8. A diagnostic probe for articular cartilage as claimed in claim 7, wherein the thickness of the articular cartilage is determined as a function of the true ultrasound speed thereof, $v_s$, which is defined by the equation:

$$v_s = 2d_s/(t_1-t_2)$$

wherein $t_{11}$ is the echo time before applying said predetermined displacement $d_s$ and $t_2$ is the echo time after applying said predetermined displacement $d_s$.

9. A diagnostic probe for articular cartilage, comprising:
a probe shaft;
an ultrasonic transducer positioned at a distal end of the probe shaft; and
a linear displacement actuator adapted to displace the ultrasonic transducer.

10. A diagnostic probe for articular cartilage as claimed in claim 9, wherein the transducer is adapted to receive an ultrasound echo.

11. A diagnostic probe for articular cartilage as claimed in claim 10, wherein the transducer is adapted to measure an ultrasound echo time.

12. A diagnostic probe for articular cartilage as claimed in claim 11, wherein the probe is further adapted to determine the thickness of articular cartilage by comparing a plurality of measured ultrasound echo times.

13. A diagnostic probe for articular cartilage as claimed in claim 12, wherein the probe is adapted to mate with a supporting arm rigidly fixed to a man-made structure.

14. A diagnostic probe for articular cartilage as claimed in claim 13, further comprising a supporting arm adapted to attach to a man-made structure.

15. A diagnostic probe for articular cartilage as claimed in claim 14, further comprising at least one strain gage mounted in proximity to the distal end of the probe shaft.

16. A diagnostic probe for articular cartilage as claimed in claim 9, wherein the ultrasonic transducer operates at a frequency of about 10 MHz.

17. A method for examining articular cartilage, comprising:
(a) contacting a surface of articular cartilage with an ultrasonic transducer;
(b) applying a predetermined displacement, $d_s$, to said surface; and
(c) determining a thickness of said articular cartilage as a function of the true ultrasound speed thereof, $v_s$, which is defined by the equation:

$$v_s = 2d_s/(t_1-t_2)$$

wherein $t_1$ is the echo time before applying said predetermined distance and $t_2$ is the echo time after applying said predetermined distance.

18. A method for examining articular cartilage as claimed in claim 17, wherein said function is:

$$h = v_s * t_1/2$$

19. A method for examining articular cartilage as claimed in claim 17, wherein said transducer preloaded with approximately 0.5 grams in said contacting step.

20. A method for examining articular cartilage as claimed in claim 17, wherein said predetermined distance is approximately 200 micrometers.

* * * * *